US00PP08118P

United States Patent [19]

van der Knapp

[11] Patent Number: Plant 8,118

[45] Date of Patent: Jan. 26, 1993

[54] CHRYSANTHEMUM PLANT — IMPROVED FUNSHINE CULTIVAR

[75] Inventor: Jacques C. M. van der Knapp, De Lier, Netherlands

[73] Assignee: Fides Beheer B.V., De Lier, Netherlands

[21] Appl. No.: 719,464

[22] Filed: Jun. 24, 1991

[51] Int. Cl.[5] ..... A01H 5/00

[52] U.S. Cl. ..... Plt./76

[58] Field of Search ..... Plt./74, 74.1, 82.1, Plt./82.4, 76, 77, 80

*Primary Examiner*—Howard J. Locker

*Attorney, Agent, or Firm*—Burns, Doane, Swecker & Mathis

[57] ABSTRACT

A new and distinct cultivar of Chrysanthemum plant named Improved Funshine is provided. The new cultivar is a spontaneous mutation of the Funshine cultivar (U.S. Ser. No. 07/719,461, filed concurrently herewith). More specifically, the new cultivar forms attractive relatively small bicolored flowers wherein the petals are white and the disc florets on the distal ends particularly towards the center bear a stronger and more intense red coloration than the Funshine cultivar (as illustrated). Also, the new cultivar exhibits more vigor than the Funshine cultivar. The inflorescence tends to be pyramidal in configuration. The response period of the flowers is approximately seven and one-half weeks. The new cultivar is particularly suited for use in the production of a cut anemone spray under greenhouse conditions.

1 Drawing Sheet

SUMMARY OF THE INVENTION

The present invention comprises a new and distinct cultivar of Chrysanthemum, botanically known as *Chrysanthemum morifolium*, Ramat., and hereinafter is referred to by the cultivar name Improved Funshine.

The new Improved Funshine cultivar is a spontaneous mutation of unknown causation which was discovered and carefully preserved during the course of plant selection work which was conducted by me. The new cultivar was discovered during June, 1987 among plants of the Funshine cultivar (U.S. Ser. No. 07/719,461, filed concurrently herewith) being grown under my direct supervision at De Lier, The Netherlands.

It was observed that a plant consistently formed bicolored flowers with white petals which included a more intense red coloration on the distal ends of the disc florets (as illustrated) than the Funshine cultivar. The plant also exhibited more vigor than the parent Funshine cultivar. All of the other characteristics of this plant were found to be substantially identical to those of the Funshine cultivar. Had I not discovered, carefully studied, and preserved this new cultivar, it would have been lost to mankind. This new cultivar is particularly well suited for growing in the production of a cut anemone spray.

It was found that the new cultivar of the present invention:

(a) exhibits attractive relatively small anemone flowers having an overall diameter of approximately 40 mm. wherein the petals are white and the disc florets particularly towards the center bear a red coloration on the distal ends which is more intense than that present on the Funshine cultivar, (b) bears flowers in a somewhat pyramidal configuration, (c) exhibits a flower response period of approximately seven and one-half weeks, (d) exhibits more vigor than the Funshine cultivar, (e) forms attractive dark green foliage, and (f) has the ability to produce flowers of commercially acceptable quality throughout the year in a cut mum production program.

Asexual reproduction of the new cultivar by cuttings as performed at De Lier, The Netherlands, in a controlled environment has demonstrated that the characteristics of the new cultivar as herein disclosed are firmly fixed and are retained through successive generations of asexual propagation.

Improved Funshine has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Funbeam cultivar (U.S. Ser. No. 07/719,463, filed concurrently herewith), it is noted that the Funbeam cultivar exhibits light red-purple petals, and even more intense coloration on the distal ends of the disc florets than the Improved Funshine cultivar. When the new cultivar of the present invention is compared to the Funrise cultivar (U.S. Ser. No. 07/719,465, filed concurrently herewith), it is noted that the Funrise cultivar exhibits red-purple petals which tend to be slightly darker than those of the Funbeam cultivar and tends to exhibit a less intense red coloration on the distal ends of the disc florets than the Improved Funshine cultivar. When the new cultivar of the present invention is compared to the Funset cultivar (U.S. Ser. No. 07/719,462, filed concurrently herewith), it is noted that the Funset cultivar exhibits very light-red petals and orange-red coloration on the distal ends of the disc florets. When the new cultivar of the present invention is compared to the Funglow cultivar (U.S. Ser. No. 07/720,211, filed concurrently herewith), it is noted that the Funglow cultivar exhibits yellow petals and greyed-purple coloration on the distal ends of the disc florets.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereinafter is The R.H.S. Colour Chart of The Royal Horticultural Society, London, England. The color values were determined at 11:00 a.m. to 12:00 noon under natural daylight conditions at De Lier, The Netherlands, during December, 1990. The plants described were grown under standard greenhouse conditions which approximate those commonly utilized for the production of cut mums.

Classification:

*Botanical.*—*Chrysanthemum morifolium* Ramat., cv. Improved Funshine.

*Commercial.*—Cut anemone spray.

Inflorescence

A. Capitulum:

*Form.*—Pyramidal.

*Type.*—Anemone.

*Diameter across face.*—Approximately 40 mm. on average.

*Diameter of flower center.*—Approximately 25 mm. on average.

B. Corolla of ray and disc florets:

*Color (General tonality from a distance of three meters).*—White with red center.

*Color ray florets (top surface).*—White, White Group 155D.

*Color disc florets.*—Red, Red Group 53B.

C. Reproductive organs:

*Androecium.*—Not present.

*Gynoecium.*—Present in both ray and disc florets.

Plant

A. General appearance:

*Height.*—Approximately 90 cm. on average.

B. Foliage:

*Color (upper surface).*—Yellow-Green Group 147A.

*Color (under surface).*—Yellow-Green Group 147B.

I claim:

1. A new and distinct cultivar of Chrysanthemum plant named Improved Funshine, substantially as herein shown and described, which:

(a) exhibits attractive relatively small anemone flowers having an overall diameter of approximately 40 mm. wherein the petals are white and the disc florets particularly towards the center bear a red coloration on the distal ends which is more intense than that present on the Funshine cultivar, (b) bears flowers in a somewhat pyramidal configuration, (c) exhibits a flower response period of approximately seven and one-half weeks, (d) exhibits more vigor than the Funshine cultivar, (e) forms attractive dark green foliage, and (f) has the ability to produce flowers of commercially acceptable quality throughout the year in a cut mum production program.

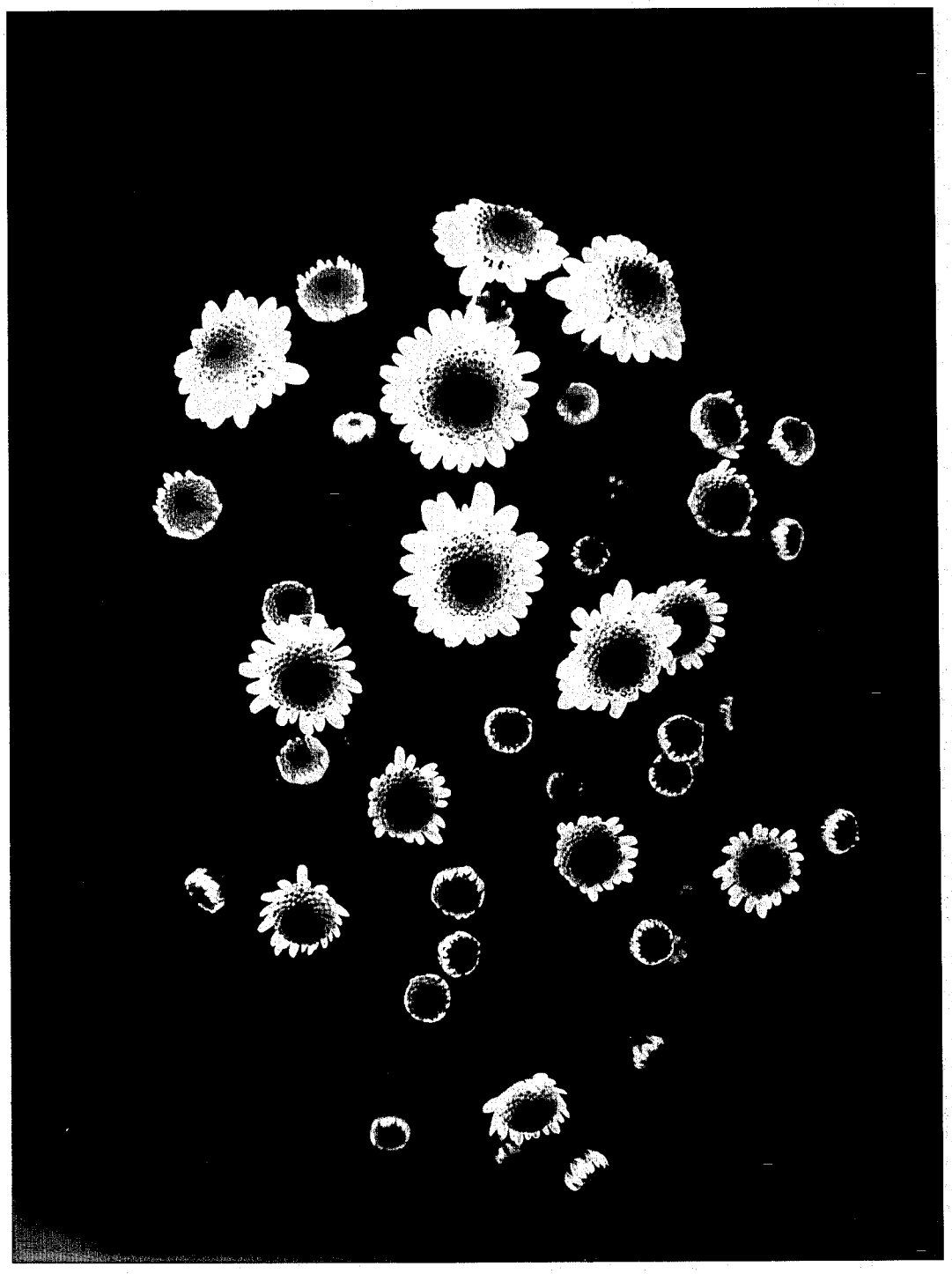

* * * * *